(12) United States Patent
Lum et al.

(10) Patent No.: US 7,056,475 B2
(45) Date of Patent: Jun. 6, 2006

(54) FLUIDICALLY ISOLATED PUMPING AND METERED FLUID DELIVERY SYSTEM AND METHODS

(75) Inventors: Paul Lum, Los Altos, CA (US); Ganapati R. Mauze, Sunnyvale, CA (US); Catherine K. Templin, Portola Valley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 570 days.

(21) Appl. No.: 10/058,797

(22) Filed: Jan. 30, 2002

(65) Prior Publication Data

US 2003/0143754 A1 Jul. 31, 2003

(51) Int. Cl.
*G01N 33/00* (2006.01)

(52) U.S. Cl. .................. 422/100; 422/99; 422/101; 422/103; 422/58; 422/68.1; 422/81; 436/180

(58) Field of Classification Search .............. 422/58, 422/61, 63, 68.1, 100, 101, 102, 103, 104
See application file for complete search history.

(56) References Cited

U.S. PATENT DOCUMENTS

| 2,625,932 | A | * | 1/1953 | Salisbury ..................... 604/7 |
| 4,065,263 | A | * | 12/1977 | Woodbridge, III ........... 422/57 |
| 4,761,381 | A | | 8/1988 | Blatt et al. |
| 5,750,906 | A | | 5/1998 | Parker et al. |
| 5,869,004 | A | | 2/1999 | Parce et al. |

\* cited by examiner

*Primary Examiner*—Yelena Gakh
*Assistant Examiner*—Sam P. Siefke

(57) ABSTRACT

An apparatus and method for pumping and optionally mixing of small quantities of biological fluid wherein the pumping mechanism is segregated from the biological fluid being pumped. The micro-pump pushes the biological fluid by compressing a cartridge housing the blood and reagents with collapsible walls with a roller or ball bearing, synchronized perpendicular plungers, or an acutely-angled member to push the biological fluid by collapsing the walls of the cartridge in the direction of flow.

17 Claims, 4 Drawing Sheets

FLUIDICALLY ISOLATED PUMPING AND METERED FLUID DELIVERY SYSTEM AND METHODS

DESCRIPTION OF THE INVENTION

1. Field of the Invention

The present invention is related to micro-fluidics, micro-pumping, and precise fluid dispensing. More particularly, the invention relates to devices and methods for microscopic pumping of blood and reagents.

2. Background of the Invention

Micro pumping for transporting small volumes of fluids is made possible by micro pumps which use piezoelectric, surface wave, thermal, fluidic or static electric actuation to move diaphragms or paddle wheels. An example of a paddle wheel type pump is described in application Ser. No. 09/976,991, Inventor: Paul Lum, entitled "A MICRO PADDLE WHEEL PUMP FOR PRECISE PUMPING, MIXING, DISPENSING, AND VALVING OF BLOOD AND REAGENTS").

These devices work in a manner similar to conventional pumps but operate on a microscopic scale. Paddle wheels operate similarly to impellers in centrifugal pumps. The impeller consists of a number of blades, either open or shrouded, mounted on a shaft that projects outside the casing. Its axis of rotation may be horizontal or vertical, to suit the fluid flow. The impeller like paddle wheel rotates increasing the momentum of the fluid by applying centrifugal force to push the fluid.

Diaphragms operate similarly to reciprocating plungers in positive-displacement pumps. The plunger passes back and forth in the chamber, whereas the diaphragm flexes back and forth. Both force a volume of fluid through the pump with each stroke. The devices are equipped with valves for the inlet and discharge of the fluid being pumped and the operation of these valves is related in a definite manner to the motions of the pistons.

The goal of a point-of-care analytical ("POC") device performing blood analysis protocols is not simply to get the blood sampled from a patient to a sensor, but to calibrate, dilute, and mix with various reagents as required by the analyte testing protocol. Dilution requires exact mixtures and ratios of blood and reagents. Calibration requires placing a standard reagent on a sensor, then removing the reagent and replacing it with a specific amount of blood or blood diluted with reagent.

The problem with the existing micro-devices is that much like conventional pumps the fluid flows through the device contaminating all the moving parts of the device. In a blood and reagent application, contaminating the pump parts requires replacing the entire pump for a new blood specimen, otherwise the blood analysis will be contaminated with remnants from earlier trials.

It is accordingly a primary object of the invention to allow the pumping and mixing of blood and reagents by segregating the pumping mechanism from the blood and reagents being pumped.

This is achieved by designing a micro-pump that pushes the blood and reagent housed in a cartridge with collapsible walls using a roller or ball bearing, synchronized perpendicular plungers, or an acutely-angled member to push the blood and reagents by collapsing the walls of the cartridge in the direction of flow.

SUMMARY OF THE INVENTION

In accordance with the invention, a micro-pumping device is simple and has the ability to pump small quantities, on the order of 1–5 micro liters, of blood and relatively larger quantities of reagents, on the order of 100–500 micro liters. The term "micro pumping" refers to pumping volumes in the range of $1\times10^{-2}$ liters to $1\times10^{-7}$ liters. The micro-pumping device has minimal fluid volume overhead or dead space, and minimizes or avoids cell lysing. The micro-pumping device minimizes electrical power consumption so that it may be incorporated in a POC device.

A first exemplary embodiment uses roller or ball bearings as in a peristaltic pump, or synchronized perpendicular plungers as in a finger pump. A second exemplary embodiment is a variation of the peristaltic pump and uses an acutely-angled member much like a "squeegee" or windshield wiper blade. Each of these embodiments generates a force applying a contained pressure to force the blood and reagents from one location to another. Henceforth, the term "biological fluid" will be used to mean bodily fluid samples, such as blood, and/or reagent chemicals; such reagents preferably support a variety of analytical methods including electrochemical, chemiluminescence, optical, electrical, mechanical and other methods, for determination of blood pH, $pO_2$, $pCO_2$, $Na^+$, $Ca^{++}$, $K^+$, hematocrit, glucose, and coagulation and hemoglobin factors. The cartridge of the present invention may be incorporated into an analytical instrument with an analytical system to conduct such electrochemical, chemiluminescence, optical, electrical, mechanical and other methods.

The first exemplary embodiment is a peristaltic micro pump. An embodiment of peristaltic micro pumping uses roller or ball bearing and transfers the fluid by either moving the cartridge over the bearing or moving the bearing over the stationary cartridge. The cartridge has at least one surface which exposes collapsible channels and reservoirs so that when the cartridge is moved over the bearings or the bearings move over the cartridge the channels and reservoirs collapse pushing the reagents in the direction of the movement.

The moving cartridge embodiment comprises slowly inserting a cartridge into a POC device with stationary bearings which rotate. A friction wheel grips the cartridge and linearly moves the cartridge to certain positions along a linear path depending on the location of the bearings. The bearings are sized to displace a measured amount of fluid. They are used to depress the collapsible channels and reservoirs. The surface of the cartridge is made of an elastic material that allows compression with relatively minimal pressure by the bearings. The depression by the bearing along with the linear motion creates a peristaltic pumping action. A volume of 1–5 micro liters of biological fluid, such as blood, and 100–500 micro liters of biological fluid, such as reagent, is displaced by the peristaltic pumping action of two different sets of bearings on the POC device each set suited for the biological fluid in the cartridge.

In an embodiment using roller bearings, different sets of bearings have different widths for the rollers depending on whether they are displacing a relatively larger or smaller volume of biological fluid. For instance blood is displaced with a narrow roller, whereas another reagent is displaced with a wide roller that covers more surface area on the cartridge and collapses a larger reservoir forcing the biological fluid into the channel corresponding to the direction of the roller motion. Alternatively, the rollers can rotate such as three rollers on a rotating arm as the cartridge moves into the POC device. The different types of biological fluid can vary the number of arms and corresponding rollers.

The advantage of the peristaltic embodiments is the isolation of the pump mechanism from the biological fluid. This segregation allows the construction of a unitary cartridge. The unitary nature of the cartridge and reusability of the bearings on the POC device make possible a system of disposable cartridges for repeated analyte detection on the same POC device. This avoids the risk of biohazard and contamination of future tests utilizing the same POC device as previous tests. Other advantages of peristaltic pumping are cleanliness, and in the case of blood assays, avoiding damage to fragile blood cells.

In another embodiment, movable bearings roll over a stationary cartridge in a configuration similar to the one discussed in the example above. The main difference being that instead of a friction wheel gripping the cartridge, the bearings inside the POC device move on predetermined paths along the surface of the cartridge. This adds an additional degree of freedom to the movement of the biological fluid using the peristaltic pumping action of the bearings to collapse the reservoirs and channels on the surface of the cartridge.

Another embodiment of a peristaltic micro pump is a pumping mechanism which uses plungers perpendicular to the pliable surface. The cartridge remains stationary and aligned with an array of small plungers which collapse the reservoir and channel walls by pressing down on the elastic surface of the cartridge so that the channel wall closes gradually in the direction of the desired fluid flow. The plungers are parallel to each other and perpendicular to the pliable surface. The plungers move in a predetermined synchronized fashion in the direction of flow. The plungers may be operated by a rotating camshaft, by individual solenoids electronically actuated in sequence, or by other methods located in the POC device. The plungers may remain depressed on the channel wall to act as a valve for back flow or may be lifted to reopen the channel in the direction opposite to the flow of the fluid. This allows the plungers to control flow in both directions. The plunger contact area (collapsor surface) is approximately the smallest incremental pumping volume (e.g. nanoliters to microliters). To scale-up to the entire cartridge containing a series of channels and reservoirs, the POC device has a battery of plunger arrays to control the transfer of biological fluid to several reaction sites for analytical measurement, and the transfer of reaction products to waste disposal. This requires programmability of the pumping system on the POC device. This embodiment of the peristaltic micro pumping does not require movement of the cartridge.

Another embodiment of a peristaltic micro pump is the "squeegee" pump. This pump consists of an stiff member angled acutely to the pliable surface in the direction of fluid flow. The member creates pressure in the direction of flow as it sweeps across the reservoirs and channels. When a member is used on a reservoir having greater width than the member, backflow becomes possible. As the member displaces fluid in the direction of the sweep, it allows back flow around the edges of waste or used fluid. This allows a biological fluid reservoir to serve as both a biological fluid and waste fluid reservoir because the laminar flow resulting from the uniform sweep would keep the biological fluid and waste fluids from mixing. Such duality of reservoir usage reduces the amount of space required on the cartridge and allows the POC device to perform more analytical tests in a limited amount of space.

Each of the embodiments discussed above serves the purpose of generating a pressure within the cartridge to transfer fluid in defined metered volumes throughout the cartridge. The pumping mechanism discussed may be used in conjunction with check valves and self-sealing membranes to valve the channel upstream of the fluid flow. Self-sealing membrane means any deformable material that mechanically collapses on itself or is collapsed by a system of valves to maintain reduced pressure conditions within said collapsed reservoirs or channels relative to ambient. The cartridge may be vented to the atmosphere in order to accommodate controlled fluid movement such as for sampling blood plasma. Alternatively, the cartridge may be designed with sample intake valves which maintain a controlled pressure within each chamber of the cartridge, such as for sampling blood gases.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate the embodiments of the invention and together with the description, serve to explain the principles of the invention.

DESCRIPTION OF THE EMBODIMENTS

Figure 1A:
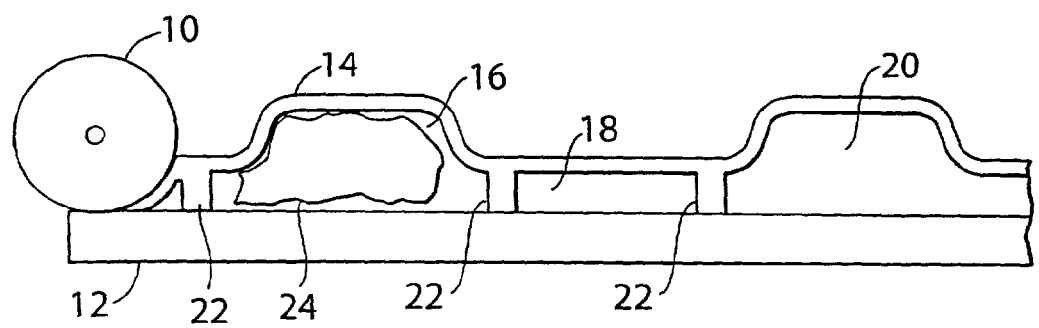
FIGS. 1A–1C are illustrations of a peristaltic micro pump using a roller bearing to collapse the pliable reservoirs and channel.

Reference will now be made in detail to the present embodiments of the invention, examples of which are illustrated in the accompanying drawings. Wherever possible, the same reference numbers will be used throughout the drawing to refer to the same or like parts.

Figure 1B:
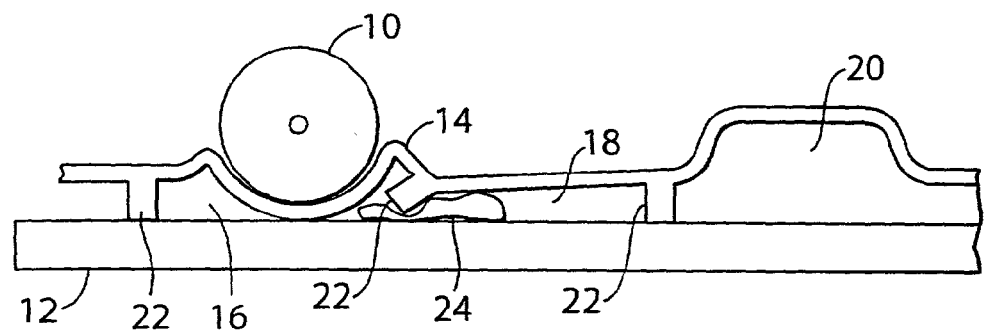
Figure 1C:
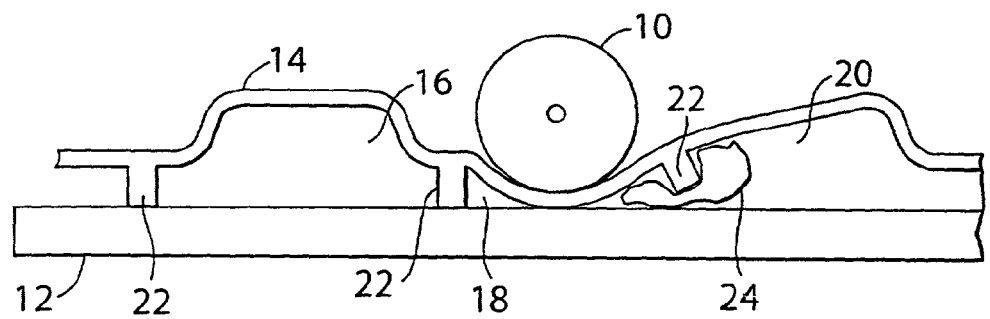

FIGS. 1A–1C illustrate the peristaltic micro pump embodiment using a roller bearing to transfer reagents by collapsing the pliable surface of the cartridge. FIG. 1A shows the roller bearing as it begins to make contact with the top surface of the cartridge. The roller bearing (10) squeezes the pliable surface (14) of the cartridge against the rigid core (12) of the cartridge that makes up the backbone of the cartridge. This rigid core (12) contains openings (not shown) which correspond to sensors on the cartridge and detectors on the POC device that enable such corresponding sensors and detectors to analyze the biological fluid (24) contained under the pliable surface (14) for analytes using methods such as optical or infra-red analysis. The pliable surface (14) may be formed of a deformable material which is elastic or inelastic as may be desired. It may be preferable to use an elastic material which assumes a more uniform shape around the roller bearing (10) and reduces deformation in advance of the motion, thus achieving a more uniform flow. The pliable surface (14) bounds filled reservoirs (16) and empty reservoirs (20) connected by channel (18). The filled reservoirs (16) are filled with biological fluid (24) which is contained in the filled reservoir (16) by check valves (22).

FIG. 1B shows the roller bearing as it collapses the pliable surface of the cartridge pushing the fluid ahead of the collapse. Roller bearing (10) collapses filled reservoir (16) pushing biological fluid (24) through channel (18). The check valve (22) behind the advancement of the roller bearing (10) stops the backflow of any biological fluid (24). The check valve (22) ahead of the advancement of the roller bearing (10) opens to allow the flow of the biological fluid (24) into the channel (18). The roller bearing (10) is connected to the POC device using a spring mechanism (not shown) which maintains a relatively uniform pressure on the roller bearing (10) while allowing the roller bearing to roll over the pliable surface (14) without tearing or puncturing the pliable surface.

FIG. 1C shows the roller bearing as it collapses the elastic surface of the cartridge pushing the fluid to a desired location. The roller bearing (10) collapses channel (18) forcing the biological fluid (24) into the empty chamber (20). The check valves (22) on either end of the channel prevent back flow. The empty chamber (20) may be used by the cartridge to mix and dilute components of the biological fluid, to calibrate the POC device with biological fluid, or to analyze a reaction between the components of the biological fluid using a sensor corresponding to the empty chamber (20) on the POC device.

Figure 2A:
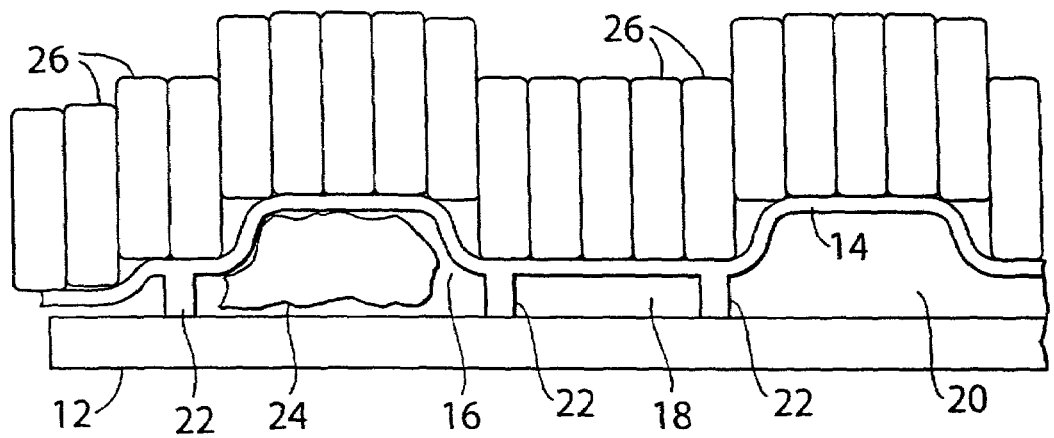
FIGS. 2A–2C are illustrations of a peristaltic micro pump using synchronized plungers to collapse the pliable reservoirs and channel.
Figure 2B:
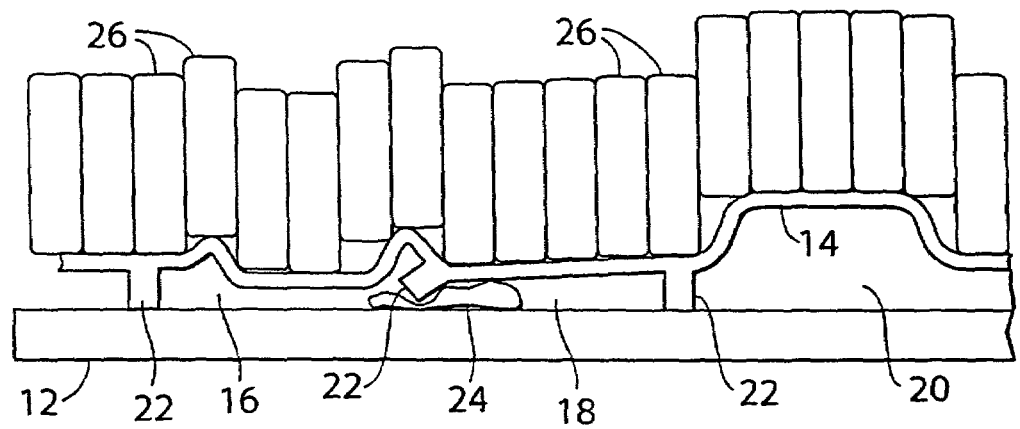
Figure 2C:
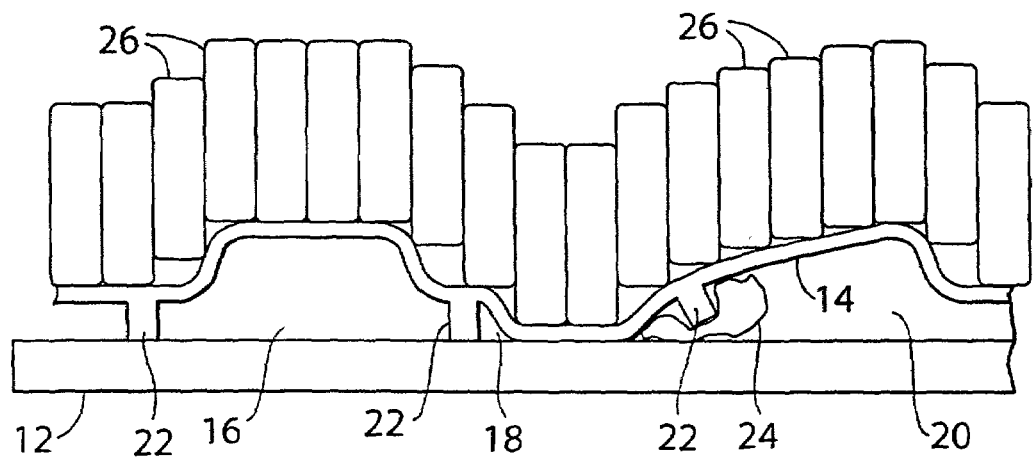

FIGS. 2A–2C illustrate the peristaltic micro pump embodiment using plungers to transfer reagents by collapsing the pliable surface of the cartridge. FIG. 2A shows the plungers (26) prior to commencing a pumping cycle on the surface of the cartridge. The plungers (26) are positioned perpendicular to the elastic membrane (14) and the rigid core (12). The biological fluid (24) is stored in the filled reservoir (16). The plungers (26) aid the check valves (22) by preventing backflow and front seepage from the filled reservoir (16). FIG. 2B shows the plungers (26) as they press down collapsing filled reservoir (16) and allowing the check valves (22) upstream to open. The plungers are connected to the POC device using a cam shaft, solenoids for electronic actuation, or other means of individually driving each plunger (26) independently of the other plungers. In one embodiment, the plungers can be operated in sequential order to push the biological fluid in one direction. FIG. 2C shows the plungers (26) as they press down and collapse the channel (18) while keeping the check valve (22) upstream of the biological fluid (24) closed. This pushes the biological fluid (24) into the empty chamber (20). Similar to the roller bearing embodiment, empty chamber (20) can serve many purposes on the POC device.

Figure 3A:
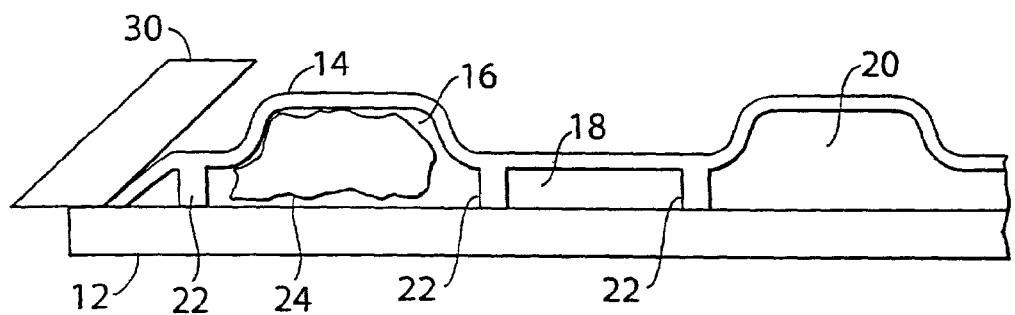
FIGS. 3A–3C are illustrations of peristaltic micro pump using an acutely-angled member to collapse the pliable reservoirs and channel.
Figure 3B:
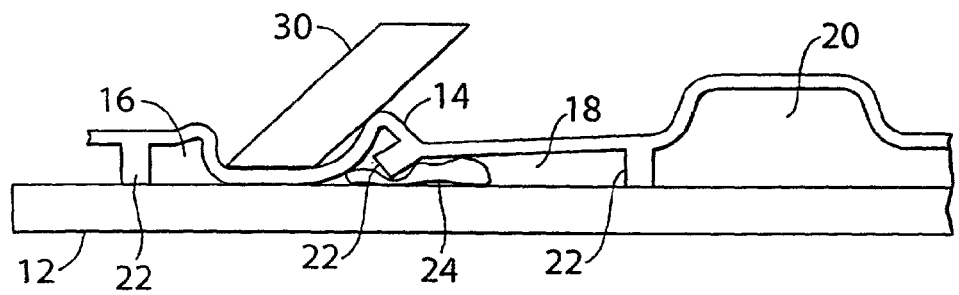
Figure 3C:
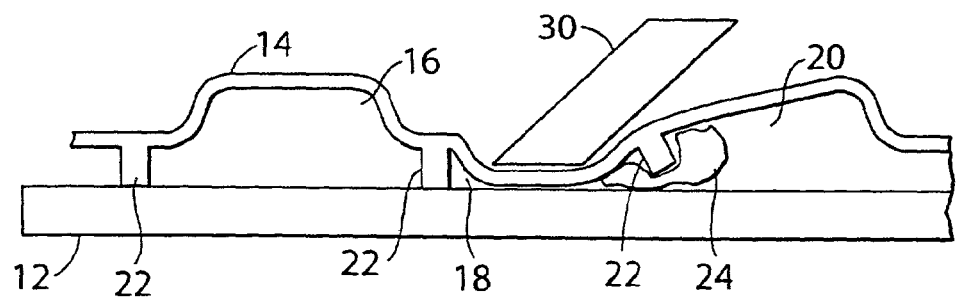

FIGS. 3A–3C illustrate the peristaltic micro pump embodiment using a acute member to transfer biological fluid by collapsing the pliable surface of the cartridge, the "squeegee" embodiment. FIG. 3A shows the acute member (30) as it begins to make contact with the top surface of the cartridge. The acute member (30) is positioned so that it has an acute angle of incidence with the pliable surface (14) and the rigid core (12) of the cartridge. The acute member (30) is connected to the POC device via a spring mechanism similar to the roller bearing embodiment, so that the acute member (30) does not tear or puncture the pliable surface (14).

FIG. 3B shows the acute member (30) as it collapses the filled reservoir (16). The check valves (22) operate similarly to the roller bearing embodiment allowing flow of the biological fluid (24) in the direction of motion and preventing backflow.

FIG. 3C shows the acute member (30) as it collapses the channel (18) and sweeps the biological fluid (24) into the empty reservoir (20). In an alternative embodiment which is not shown, acute member sweeps across empty reservoir. The width across the cartridge of the acute member is less than the corresponding width of the empty reservoir. When the acute member sweeps across the empty reservoir it does not collapse the entire reservoir as it collapsed the filled reservoir. The acute member, thereby mixes the biological fluid now contained in the empty reservoir. Where components of the biological fluid react with each other, the sweep of the acute member serves to further the reaction by mixing and forcing the components of the biological fluid into contact with each other, and allowing the reaction products to backflow through the empty reservoir around the edges of the acute member.

Figure 4:
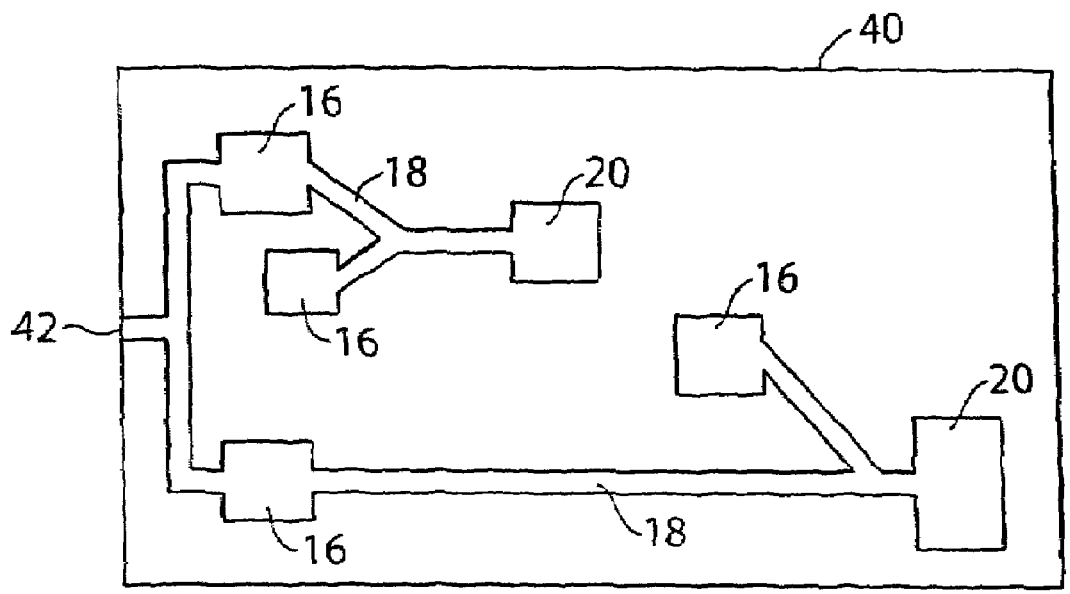
FIG. 4 is an illustration of a configuration for the cartridge allowing for several peristaltic micro pumps to transfer biological fluid throughout a network of reservoirs and channels.

FIG. 4 illustrates an example of a cross-section of the cartridge showing the network of channels and reservoirs. The cartridge (40) contains a series of filled reservoirs (16) and empty reservoirs (20) connected by channels (18). The biological fluid intake (42) serves as supply for the filled reservoirs (16) which contain biological fluid which is sampled and inserted into the cartridge, as opposed to the biological fluid that is stored in the filled reservoirs (16) when the cartridge (40) is manufactured. The means for collapsing the elastic surface of the cartridge whether by roller or ball bearing or acutely-angled member can be a single unit stretching across the cartridge requiring strategic placement of filled reservoirs (16) for reagents to accomplish the appropriate sequence of analysis, such as by a staggered array of channels and reservoirs. Also a unitary collapsing means requires predetermined volumes for the filled reservoirs (16) so that proper dilutions and resulting concentrations are achieved for the analytes to be examined. Such considerations apply if the unitary collapsing means is used on a stationary cartridge or the cartridge is pulled across a stationary unitary collapsing means.

The cartridge may be pulled by a motor in the POC device or manually pushed by operator of the POC device. The incremental placement of the reservoirs also allows for control of the dwell time or mixture time in the empty reservoirs (20). The motor pulling the cartridge into the POC device has a switch to detect the presence of the cartridge (40) entering biological fluid intake (42) end first. The motor has wheels that "grip" the cartridge and pull it into the POC device and across the unitary collapsing means. This gives the POC device control over the rate of cartridge insertion by modulating the current to the motor and controlling the dwell time.

In an alternative embodiment, the collapsing means consist of several sets of roller or ball bearings or acute members. These collapsing means are either staggered within the POC device or capable of being individually controlled. If staggered within the POC, then a "grip" motor mechanism as described above pulls the cartridge (40) across these staggered collapsing means. This allows another degree of freedom to the number of possible reactions and dwell times based on the placement and orientation of the filled reservoirs (16) and empty reservoirs (20) and network of channels (18). The "grip" motor is also capable of going in the reverse direction and using the collapsing means as prevent backflow and allow for more detailed manipulation of the biological fluid (24).

The plunger embodiment of the peristaltic micro pump allows for a stationary cartridge inserted into the POC device. The plungers (26) are arranged in an array across the dimensions of the cartridge (40). They are used to "massage" the pliable surface of the cartridge and transport the reagents from filled reservoirs (16) to empty reservoirs (20) through channels (18).

Figure 5:
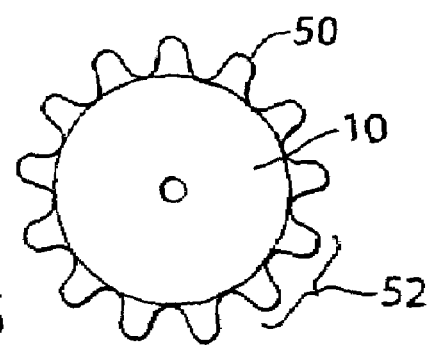
FIG. 5 is an illustration of a roller bearing with protrusions to measure the volumes of displaced biological fluid.

FIG. 5 illustrates an alternative embodiment for the roller bearing described previously which is capable of precise volume displacement. The roller bearing (10) has protrusions (50) along its circumference that comes in contact with the pliable surface (14) of the cartridge arranged so that they are evenly spaced and capture a measured volume (52) between each pair of protrusions (50). The protrusions (50) may be disposed in a variety of other ways to allow a predetermined measuring out of a predetermined volume of biological fluid. This volume may be specified so that a known volume is transferred with each revolution of the roller bearing (10).

The roller bearing of FIG. 5 works similarly to a paddle wheel which may be configured to sweep a predetermined volume with each revolution. The principal difference being that a paddle wheel contacts the biological fluid, whereas the roller bearing in this embodiment does not contact the biological fluid. Instead, the protrusions (50) create concavities in the pliable surface (14) which contain a predetermined volume of biological fluid as the roller bearing (10) collapses the pliable surface (14) against the rigid core (12).

In the peristaltic embodiments described, the cartridge may be designed as a three dimensional matrix of pliable surfaces which deform under the collapsor, whether such collapsor is roller or ball bearing, plunger, or acutely-angled member. The term "collapsor" refers to any means of compressing the pliable surface of the cartridge against rigid core including, but not limited to, roller or ball bearings, plungers, or acutely-angled members. The collapsor applies a compression force on the pliable surface which collapses because of the adjacent rigid surface which makes up the core of the cartridge. This allows the pliable surfaces that do not come into contact with the collapsor to bow and maintains the integrity of the cartridge matrix such that the collapsor surface (portion of collapsor that comes in to contact with the pliable surface) does not rip or tear the matrix.

The cartridge comprises a pliable surface. The pliable surface comprises of deformable material which may comprise a composition of elastomer, plastic, or other polymeric material. In one embodiment, the pliable surface can be one side of an envelope of pliable material one side of which forms the pliable surface of the cartridge. This envelope contains the biological fluid and bounds the reservoirs and channels. The cartridge is assembled by attaching one side of this envelope to the rigid core of the cartridge. The cartridge can be sized to fit into an hand-held POC device or larger device to conduct analysis of the biological fluid.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A micro pumping device for transporting small volumes of biological fluid comprising:
    a collapsor that delivers a compressive force to a deformable material, said collapsor comprising at least one bearing chosen from roller bearings and ball bearings; and
    a cartridge adapted to receive at least one biological fluid, said cartridge including:
        at least one pliable surface, said pliable surface comprising said deformable material which collapses in response to a compression force delivered from said collapsor; and
        a rigid core adjacent to said pliable surface and opposite said collapsor, said rigid surface adapted to aid said collapsor in collapsing said pliable surface;
    wherein said collapsor comprises a collapsor surface with protrusions having predetermined spacing, said predetermined spacing creating corresponding concavities in said pliable surface as said collapsor collapses said pliable surface against said rigid core, displacement from said corresponding concavities thereby causing a predetermined amount of biological fluid to be delivered from the cartridge.

2. A micro pumping device according to claim 1 wherein: said collapsor comprises roller bearings.

3. A micro pumping device according to claim 1 wherein: said collapsor surface comprises a circumference of said bearing; said protrusions disposed at predetermined locations about said circumference such that each adjacent pair of protrusions defines a correspondingly predetermined volume.

4. A micro pumping device according to claim 3 wherein: said cartridge comprises at least one component chosen from reservoirs, channels, and valves, wherein said component contains the flow of said biological fluid.

5. A micro pumping device according to claim 1 wherein: said network comprises a system of check valves preventing backflow through said reservoirs and channels.

6. A micro pumping device according to claim 5 wherein said device further comprises a network comprising staggered channels and reservoirs such that motion in one direction by said collapsor results in a sequential collapse of said staggered channels and reservoirs.

7. A micro pumping device according to claim 5 wherein said deformable material comprises a self-sealing membrane.

8. A micro pumping device according to claim 5 wherein said cartridge comprises at least one component chosen from reservoirs, channels, and valves, wherein said component contains the flow of said biological fluid.

9. A micro pumping device according to claim 8 wherein said device further comprises a network comprising staggered channels and reservoirs such that motion in one direction by said collapsor results in a sequential collapse of said staggered channels and reservoirs.

10. A micro pumping device according to claim 9 wherein said deformable material comprises a self-sealing membrane.

11. A micro pumping device according to claim 1 wherein said cartridge comprises at least one component chosen from reservoirs, channels, and valves, wherein said component contains the flow of said biological fluid.

12. A micro pumping device according to claim 1 wherein said device further comprises a network comprising staggered channels and reservoirs such that motion in one direction by said collapsor results in a sequential collapse of said staggered channels and reservoirs.

13. A micro pumping device according to claim 12 wherein said deformable material comprises a self-sealing membrane.

14. A micro pumping device according to claim 13 wherein said network comprises check valve means for preventing backflow through said reservoirs and channels.

15. A micro pumping device according to claim 1 wherein said deformable material comprises a self-sealing membrane.

16. A mico pumping device according to claim 15 wherein said network comprises check valve means for preventing backflow through said reservoirs and channels.

17. A micro pumping device according to claim 3 wherein said deformable material comprises a self-sealing membrane.

* * * * *